US010568831B2

(12) United States Patent
Mendenhall et al.

(10) Patent No.: US 10,568,831 B2
(45) Date of Patent: Feb. 25, 2020

(54) METHOD TO ENHANCE SWALLOWING SAFETY AND APPEAL OF BEVERAGES FOR TREATING DYSPHAGIA BASED ON RHEOLOGICAL AND SENSORY PARAMETERS

(71) Applicants: Wisconsin Alumni Research Foundation, Madison, WI (US); Regents of the University of Minnesota, Minneapolis, MN (US)

(72) Inventors: Heather N. Mendenhall, Madison, WI (US); Richard W. Hartel, Madison, WI (US); JoAnne Robbins, Madison, WI (US); Jacqueline A. Hind, Madison, WI (US); Zata M. Vickers, St. Paul, MN (US)

(73) Assignees: Wisconsin Alumni Research Foundation, Madison, WI (US); The Regents of the University of Minnesota, Minneapolis, MN (US)

( * ) Notice: Subject to any disclaimer, the term of this patent is extended or adjusted under 35 U.S.C. 154(b) by 566 days.

(21) Appl. No.: 13/804,781

(22) Filed: Mar. 14, 2013

(65) Prior Publication Data
US 2014/0004045 A1 Jan. 2, 2014

Related U.S. Application Data

(60) Provisional application No. 61/665,995, filed on Jun. 29, 2012.

(51) Int. Cl.
| | |
|---|---|
| A23L 33/10 | (2016.01) |
| A61K 47/00 | (2006.01) |
| A23L 2/38 | (2006.01) |
| A61K 9/00 | (2006.01) |
| A23L 33/00 | (2016.01) |
| A61B 5/00 | (2006.01) |
| A61K 49/04 | (2006.01) |
| A61B 5/03 | (2006.01) |

(52) U.S. Cl.
CPC .............. *A61K 9/0053* (2013.01); *A23L 2/38* (2013.01); *A23L 33/10* (2016.08); *A23L 33/30* (2016.08); *A23L 33/40* (2016.08); *A61B 5/038* (2013.01); *A61B 5/4205* (2013.01); *A61K 9/0056* (2013.01); *A61K 9/0095* (2013.01); *A61K 47/00* (2013.01); *A61K 49/0404* (2013.01)

(58) Field of Classification Search
CPC .... A61K 9/0053; A61K 47/00; A61K 9/0095; A61K 9/0056; A23L 33/10; A23L 33/40; A23L 33/30; A23L 2/38; A61B 5/038
See application file for complete search history.

(56) References Cited

U.S. PATENT DOCUMENTS

| 4,020,152 A | 4/1977 | Heitz |
| 5,932,235 A | 8/1999 | Ninomiya et al. |
| 5,976,084 A | 11/1999 | Tymchuck |

FOREIGN PATENT DOCUMENTS

| WO | WO 2004/069179 A2 | 8/2004 |
| WO | 2013/087918 A1 | 6/2013 |

OTHER PUBLICATIONS

Garcia et al. Managing Dysphagia Through Diet Modifications, Evidence-based help for patients with impaired swallowing, AJN. Nov. 2010. vol. 110, No. 11; p. 26-30.*
Adams & Birdsall (1946) New Consistometer Measures Corn Consistency, *Food Industries* 78-80.
Adeleye, B., & Rachal, C. (2007) Comparison of the rheological properties of ready-to- serve and powdered instant food-thickened beverages at different temperatures for dysphagic patients. *Journal of the American Dietetic Association*, 1 0 7 ( 7), 1176-1182.
Aime, D., Arntfield, S., Malcolmson, L., and Ryland, D. (2001) Textural analysis of fat reduced vanilla ice cream products. *Food Research International*, 34 (2-3), 237-246.
Bourne, M. C. (2002) *Food texture and viscosity: concept and measurement*. Academic Pr., San Diego, CA. Ch 7: 257-280.
Cutler, A.N., Morris, E.R. And Taylor, L.J. 1983. Oral perception of viscosity in fluid foods and model systems. *J. Texture Studies* 14, 377-395.
Germain I., Dufresne, T. and Ramaswamy, H.S., 2006, Rheological characterization of thickened beverages used in the treatment of dysphagia, *Journal of Food Engineering*, 73, 64-74.
Hind, J. A., Nicosia, M. A., Gangnon, R., and Robbins, J. A. (2005) the effects of intraoral pressure sensors on normal young and old swallowing patterns. *Dysphagia*, 20 (4), 249-253.
Hootman, R. C. (1992) *Manual on descriptive analysis testing for sensory evaluation*. ASTM International, Philadelphia: ASTM. p. 52.
Houska, M., Valentova, H., Novotna, P., Strohalm, J., Sestak, J., & Pokorny, J. (1998). Shear rates during oral and nonoral perception of viscosity of fluid foods. J Texture Studies 29(6):603-15.
Li et al (1992) Viscosity Measurements of Barium, Sulfate Mixtures for Use in Motility Studies of the Pharynx and Esophagus, *Dysphagia* 7:17-30.
Lotong, V., Chun, S., Chambers, E., and Garcia, J. (2000) Texture and flavor characteristics of beverages containing commercial thickening agents for dysphagia diets. *Journal of Food Science*, 68 (4), 1537-1541.
Macfie, H. J., Bratchell, N., Greenhoff, K., and Vallis, L. V. (1989) Designs to balance the effect of order of presentation and first-order carry-over effects in hall tests. *Journal of Sensory Studies*, 4 (2), 129-148.

(Continued)

*Primary Examiner* — Michael G. Hartley
*Assistant Examiner* — Nabila G Ebrahim
(74) *Attorney, Agent, or Firm* — Joseph T. Leone, Esq.; DeWitt LLP

(57) ABSTRACT

An edible composition of matter having an apparent viscosity of from about 150 cP to about 2000 cP at about 30 s−1; a yield stress of from 0 Pa to about 20 Pa at 1 s$^{-1}$; and a flow index of from about 0.2 to about 0.6. The composition may include an imaging agent. The compositions are useful for providing sustenance to dysphagic subjects and for evalualuating dysphagia.

10 Claims, 10 Drawing Sheets

(56) References Cited

OTHER PUBLICATIONS

Matta, Z., Chambers IV, E., Garcia, J. M., and Helverson, J. M.G. (2006) Sensory characteristics of beverages prepared with commercial thickeners used for dysphagia diets. *Journal of the American Dietetic Association,* 106 (7), 1049-1054.

Mills, R. (1999) Rheology overview: Control of liquid Viscosities in dysphagia management. *Nutrition in Clinical Practice, 14* (5), (suppl): S52-S56.

Nicosia, M.A., Hind, J. A., Roecker, E. B., Carnes, M., Doyle, J., Dengel, G. A., and Robbins, J. A. (2000) Age effects on the temporal evolution of isometric and swallowing pressure. *Journals of Gerontology Series A: Biological and Medical Sciences,* 55 (11), M634-M640.

O'Leary, M., Hanson, B., and Smith, C. 2010. Viscosity and non-Newtonian features of thickened fluids used for dysphagia therapy. Journal of Food Science. 75 (6) E330-E338.

Pelletier, C. A. (1997) A comparison of consistency and taste of five commercial thickeners. *Dysghagia,* 12 (2), 74-78.

Pelletier, C. A., & Lawless, H. T. (2003) Measuring taste acceptance i1 neurologically impaired adults. *Food Quality and Preference,* 14 (7), 595-602.

Pouderoux, P., & Kahrilas, P. J. (1995) Deglutitive tongue force modulation by volition, volume, and viscosity in humans. *Gastroenterology,* 108 (5), 1418-1426.

Rao, M. A. (1977) Rheology of liquid foods- a review. *Journal of Texture Studies,* 8 (2), 135-168.

Scott, M., Hill, F., Norris, L., and Heuser, G. (1946) Chemical determination of riboflavin. *Journal of Biological Chemistry,* 165 (1), 65 -71.

Shaker, R., Cook, I. J. S., Dodds, W. J., and Hogan, W. J. (1988) Pressure-flow dynamics of the oral phase of swallowing. *Dysphagia,* 3 (2), 79-84.

Shama F, and Sherman P. 1973. Identification Of Stimuli Controlling The Sensory Evaluation Of Viscosity Ii. Oral Methods. *J Texture Stud* 4(1):111-8.

Sherman, P. 1982.Hydrocolloid solutions and gels. Sensory evaluation of some textural characteristics and their dependence on rheological properties. Progress in Food and Nutrition Science 6 266-284.

Stanek, K., Hensley, C., and Van Riper, C. (1992) Factors affecting use of food and commercial agents to thicken liquids for individuals with swallowing disorders. *Journal of the American Dietetic Association (USA)* 92:488-490.

Szczesniak, A. S. (1963) Classification of Textural Characteristics. *Journal of Food Science, 28* (4), 385-389.

Szczesniak, A. (1990) Psychorheology and texture as factors controlling the consumer acceptance of food. *Cereal Foods World (USA)* 35: 1201-1205.

U.S. Census Bureau. *Populations Projections Program. Washington, DC: Department of Commerce, Population Division, Jan. 2000* (Copy Not Provided).

Wood, F. W. (1968) Psychophysical Studies on the consistency of liquid foods. Rheology and Texture of Foodstuffs, SCI Monograph, No. 27, p. 40.

Garcia et al., (2010) Managing Dysphagia Through Diet Modifications, AJN, vol. 110, No. 11, 26-33.

\* cited by examiner

METHOD TO ENHANCE SWALLOWING SAFETY AND APPEAL OF BEVERAGES FOR TREATING DYSPHAGIA BASED ON RHEOLOGICAL AND SENSORY PARAMETERS

CROSS-REFERENCE TO RELATED APPLICATIONS

Priority is hereby claimed to provisional application Ser. No. 61/665,995, filed Jun. 29, 2012, which is incorporated herein by reference.

FEDERAL FUNDING STATEMENT

This invention was made with government support under 2009-55503-05206 awarded by the USDA/NIFA. The government has certain rights in the invention.

FIELD OF THE INVENTION

The invention is directed to edible formulations for evaluating and treating dysphagic patients and to provide methods to gauge the rheological properties of modified foods to assess their suitability for use with dysphagic patients.

BACKGROUND OF THE INVENTION

The oropharyngeal physiology involved in a normal swallow is an exceedingly complex series of coordinated actions. A host of very different medical conditions, both physical and neurological in nature, can alter normal swallowing. For example, patients suffering stroke, Alzheimer's disease, amyotrophic lateral sclerosis, or traumatic brain injury can exhibit abnormal swallowing. In many instances, the abnormal swallow can and does cause aspiration of food material, both liquids and solids, into the lungs. This is especially prevalent (and life-threatening) in frail patients and in elders. Aspiration of foreign material into the airways leads to increased morbidity in hospitalized patients and can lead to pneumonia. Abnormalities in the human swallow, whether or not the condition results in aspiration of foods, is called dysphagia.

A normal human swallow can be separated into four semi-distinct phases: 1) oral preparation; 2) the oral phase; 3) the pharyngeal phase; and 4) the esophageal phase. Patients who have suffered a stroke, traumatic brain injury, or neuromuscular disorder (such as MS or ALS) have an increased risk of aspiration, and may have difficulty with the oral phase, the pharyngeal phase, or both. Weak or uncoordinated muscle movement when chewing (or in the initial oral phase of swallowing) can cause food to be propelled or fall into the pharynx and into the open airway. This often occurs before the completion of the oral phase of swallowing. Or impaired propulsion can result in residue in the oral cavity, valleculae, or pharynx after the swallow, when the residue may be inhaled into the trachea. Or a delay in the onset of the pharyngeal swallowing response can result in food falling into the airway during the delay when the airway is open. Or reduced peristalsis in the pharynx can leave residue in the pharynx after the swallow is completed that can fall or be inhaled into the airway. Additionally, laryngeal or cricopharyngeal dysfunction can also lead to aspiration because of decreased closure of the airway during swallowing. Any of these conditions, or a combination of these conditions, can lead to aspiration of food or liquids into the airways.

While the standard bedside swallow exam to screen patients is beneficial for evaluating patients at risk for dysphagia, it sheds very little light on the whether the patient is actually aspirating and even less light on the biomechanical etiology of the defect arises. Many patients, due to concomitant neurological defects effecting the sensory response, will silently aspirate, giving no indication (e.g. cough) during the clinical/non-instrumental exam as to their condition. Aspiration in dysphagic patients, however, can be detected using a radiographic modified barium swallow fluoroscopic examination. Videofluoroscopy of the swallow mechanism using barium for its radio-opacity is performed as routine practice to elucidate more clearly the anatomical or neurological deficit causing the dysphagia and the impact of those deficits on bolus transit or flow.

Dynamic fluoroscopic evaluation of the swallow, however, is not without its attendant difficulties and shortcomings. For instance, the imaging compositions conventionally used for fluoroscopic exams are thick suspensions of barium sulfate. Barium is employed because of its large X-ray absorption cross-section, which makes it radio-opaque. The use of barium sulfate suspensions as a radiological contrast medium has a number of drawbacks. A first drawback is that conventional barium sulfate suspensions generally have either poor adhesion to the walls of the oropharynx or too much adhesion. These compositions, having been initially designed to image the gastrointestinal tract, have not been altered much, if any, for use in imaging the mouth and throat. If the walls of the oropharyngeal tract are not sufficiently coated with the contrast agent, an X-ray image cannot be generated; there simply is not enough contrast to visualize the relevant structures. Conversely, if the suspension is made thicker to encourage adhesion, the thick, chalky suspension actually coats the mouth and throat and physically alters the movement of the muscles used for swallowing. Consequently, the image generated is not necessarily indicative of the true swallow response exhibited by the patient. Further, total clearance of material from the oropharyngeal and esophageal cavities would be a useful visual cue to determine whether the function of these structures is within normal limits. If the oropharynx is coated with too much contrast agent, the dense X-ray cross-section creates a complete opacity in the resultant X-ray exposure, which does not provide sufficient detail of the structures involved in swallowing. A complicating factor is the taste and chalky texture of barium suspensions, which makes them generally unpleasant to hold in the mouth and to swallow. Substances that are more food-like in taste and texture would more likely elicit a more representative swallow response.

See, for example, U.S. Pat. No. 4,020,152 to Heitz, which describes barium titanate and barium zirconate X-ray contrast agents. This patent specifically notes that it is quite difficult to generate fluoroscopic images of the oropharyngeal cavity. Heitz states that patients have great difficulty in holding a mouthful of contrast medium at the very back of their throats for a long time without swallowing. When the patient swallows the barium sulfate suspension, it slides over the mucous membranes, often without leaving sufficient contrast agent in place to generate an image. Heitz believes the lack of adhesion is due to the saliva covering the walls of the oropharynx, which substantially reduces the adherence of a barium sulfate suspension. As a result, radiological examination of this key physiological intersection, the junction where aspiration occurs, is difficult and often leads to only mediocre imaging. Failure to generate a clean radiological image of the swallow leads to imprecise diagnosis and treatment.

Moreover, once a patient has been diagnosed as having dysphagia and is known to be aspirating foods, some compensatory treatment must be implemented to prevent further aspiration. One method widely employed is to alter the consistency (i.e., the viscosity) of liquids. Thickened liquids have been shown to inhibit aspiration by increasing bolus transit time, providing more time for airway closure providing greater "mouthfeel" and by providing greater mechanical resistance to the muscles involved in swallowing and to. See, for example, U.S. Pat. No. 5,932,235, to Ninomiya et al.: This patent describes a jellied preparation containing carrageenan, locust bean gum, and a polyacrylic acid. The preparation can be used to thicken liquid foodstuffs.

In hospital, nursing home, and clinical settings, thickened liquids deemed to be "nectar thick" or the more viscous "honey thick"are provided to dysphagic patients. For instance, preferred liquid foods such as milk, coffee, or tea are thickened with an added thickening agent prior to being fed to a dysphagic subject. However, there has not been implemented any objective set of criteria to define the levels of thickness/viscosity which constitute a nectar thick composition versus a honey thick composition. The health provider simply thickens the desired food to a subjective thickness and provides it to the patient. This lack of standardization fosters great variability in practice. In short, individual speech pathologists, dieticians, food service managers, and food manufacturers arbitrarily determine, based upon their own subjective evaluation, what constitutes a nectar thick composition and a honey thick composition. In the vast majority of instances, no objective measurement of the increased viscosity of the modified food is taken. If a measurement is taken, it is done using rough, empirical evaluations of viscosity, such as the Line Spreading Test (LST), a test developed in the 1940s to gauge the consistency of foods. See Grawemeyer, E. A. and Pfund, M. C. (1943) Line spread as an objective test of consistency," Food Research 8:105-108. This greatly hinders gathering detailed information on the efficacy of using thickened liquids in the treatment of dysphagia.

Dysphagia is associated with increased mortality and morbidity, including malnutrition, dehydration, pulmonary complications, and reductions in quality of life. These sequelae cost millions of healthcare dollars in hospitalizations, outpatient visits and increased need for supported care. It is estimated that over 18 million adults and millions of children in the United States are dysphagic. As noted above, people suffering from dysphagia are diagnosed radiographically using standardized barium fluids. One common treatment strategy identified from the diagnostic evaluation is the need for patients to drink thickened liquids to prevent misdirection of fluids into the airway. The commercially available diagnostic fluids (available from providers such as Bracco Diagnostics, Inc., Princeton, N.J. USA and Bracco Imaging SpA, Milan, Italy) are characterized by an apparent viscosity at 30 s−1 as nectar (~300 cP), thin honey (~1,500 cP) or honey (~3,000 cP). Apparent viscosity is the standard measure against which thickened fluids are typically measured. However, commercially-available thickened beverages, which are supposedly based on the standards of viscosity set by the diagnostic fluids, vary greatly from the apparent viscosity of the commercially available diagnostic fluids.

Therefore, there continues to be a long-felt and unmet need in the study and treatment of dysphagia for a standardized set of edible compositions for both the gross evaluation of dysphagia and for a corresponding viscosity-standardized set of edible compositions, either with a radio-opaque agent for use in the radiographic imaging of the mouth and throat, or without a radio-opaque agent for providing satisfying sustenance to dysphagic individuals.

SUMMARY OF THE INVENTION

Disclosed is an edible composition of matter having an apparent viscosity of from about 150 cP to about 2000 cP at about 30 $s^{-1}$; a yield stress of from 0 Pa to about 20 Pa at 1 $s^{-1}$; and a flow index of from about 0.2 to about 0.6. The composition may also have an apparent viscosity from about 200 cP to about 2000 cP, a yield stress of from 0 to about 15 Pa, and a flow index from about 0.3 to about 0.5. The composition may also have an apparent viscosity of from about 250 cP to about 1800 cP, a yield stress of from 5 to about 14 Pa, and a flow index of from about 0.3 to about 0.5. The apparent viscosity of the edible composition may be from about 250 cP to about 1800 cP, the yield stress from 0 to about 2 Pa, and the flow index from about 0.3 to about 0.5.

In another version, the edible composition has an apparent viscosity of from about 200 cP to about 500 cP (again at about 30 $s^{-1}$), a yield stress of from 0 to about 2 Pa at 1 $s^{-1}$, and a flow index of from about 0.3 to about 0.5. Here, the apparent viscosity may also be from about 250 cP to about 400 cP, or from about 270 cP to about 330 cP. In another version, the edible composition may have an apparent viscosity of from about 1200 cP to about 1800 cP (at about 30 $s^{-1}$), a yield stress of from 5 to about 14 Pa, and a flow index is from about 0.3 to about 0.5. The apparent viscosity may be from about 1250 cP to about 1700 cP, or from about 1400 cP to about 1600 cP.

Any of the above-described edible compositions may further comprise an imaging agent. The imaging agent may comprise a radio-opaque imaging agent. The radio-opaque imaging agent may comprise a barium-containing compound, such as, but not limited to, barium sulfate.

Also disclosed herein is a method of providing sustenance to a dysphagic subject. The method comprising feeding to the subject one or more edible compositions described hereinabove.

Additionally disclosed herein is a method for evaluating a human subject for dysphagia. The method comprises providing at least one edible composition as described herein to a subject to be evaluated for dysphagia, and then evaluating swallowing in the subject for indications of dysphagia during and after the subject swallows at least one edible composition.

DETAILED DESCRIPTION

Figure 1:
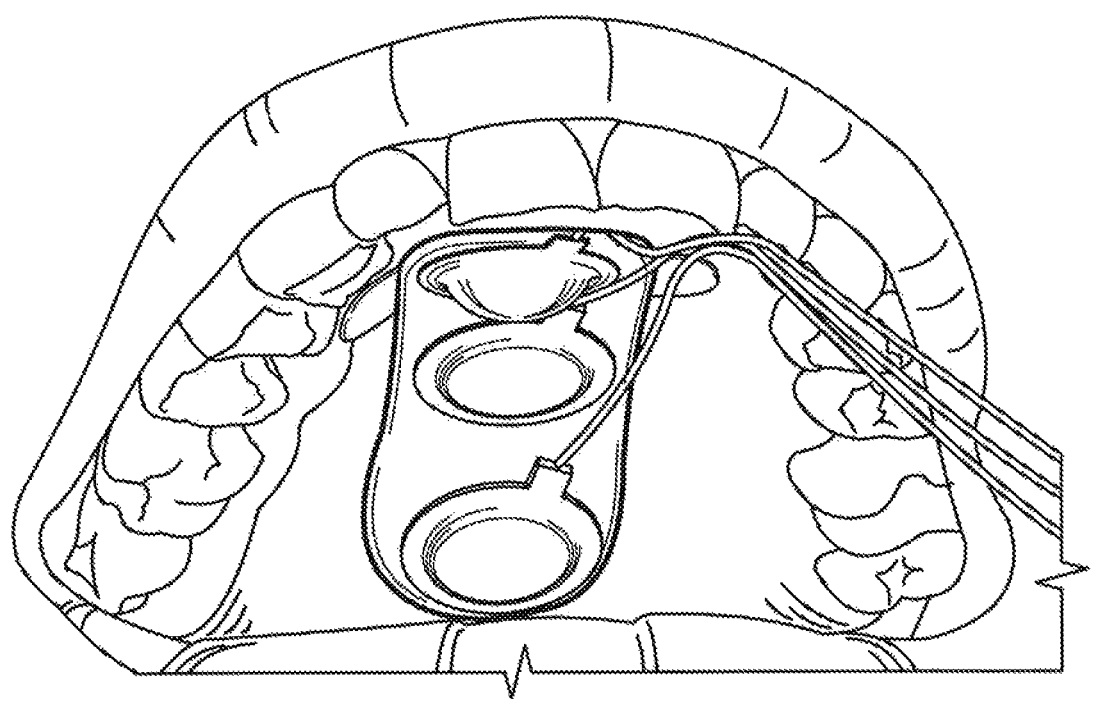
FIG. 1 is a photograph of a bulb pressure array affixed to the hard palate of a subject's mouth at the midline. See the Examples for a detailed description.

As noted earlier, apparent viscosity is the standard measure against which thickened fluids are typically measured. However, commercially-available thickened beverages, which are supposedly based on the standards of viscosity set by the commercially available diagnostic fluids, vary greatly from the apparent viscosity of, for example, the commercially available "VARIBAR"®—brand fluids.

The present inventors have found that characterizing a fluid by its apparent viscosity is, by itself, insufficient to describe accurately and adequately the functionality of a thickened fluid. It has been found that whether a thickened fluid is perceived as satisfying and refreshing, with little to no mouth-coating, depends on other rheological parameters in addition to apparent viscosity. Thus, the crux of the present method is to identify these additional rheological parameters and to define the suitable ranges of these parameters that are key to developing thickened fluids that are safe to drink and satisfying to the subject. In other words, the conventional approach relies entirely upon apparent viscosity as the sole criterion by which thickened edible fluids are measured. The present inventors, however, have established other, results-effective rheologic variables that yield thickened fluids that are both safer for dysphagic subjects to consume and satisfying to the palate.

There are many ways to characterize fluid rheology. The following approach was chosen based on two primary stages of swallowing. First, as an individual holds a liquid bolus in the oral cavity, very low shear rate is applied to the boluses he/she prepares to swallow. The viscosity at very low shear rates (<1 $s^{-1}$) is similar to a yield stress ($\sigma_o$), or the force required to initiate motion of the fluid from rest. A certain amount of yield stress helps to prevent uncontrolled flow of the fluid toward the airway, until the oral mechanisms, including the tongue, provide sufficient force to initiate controlled flow. Secondly, once a swallow is initiated, the range of shear rates important in the mouth is from about 1 $s^{-1}$ to about 100 $s^{-1}$. It is within this rough range where many thickened fluids exhibit shear-thinning behavior. In this range of shear rates, the apparent viscosity of shear thinning fluids decreases with increasing shear rate. This shear thinning under shear flow plays a role in reducing the apparent viscosity of the fluid during the swallow, making it easier to completely clear the fluid from the mouth during the swallow.

A Hershel Bulkley rheological model can be used to characterize fluids in this range:

$$\sigma = k\gamma^n + \sigma_0$$

Here, $\sigma$ is shear stress, $\gamma$ is shear rate, k is the consistency coefficient and n the flow index, and $\sigma_0$ the yield stress. According to the present method and composition, four parameters are needed to define a biophysically-designed fluid with ideal swallowing characteristics. That is, the fluid must be refreshing, leave minimal mouth coating, yet be sufficiently cohesive, with advantageous flow rate precluding aspiration into the airway. The critical rheological parameters are apparent viscosity (measured at about 30 $s^{-1}$ to be consistent with the "VARIBAR"®-brand standards), yield stress (or viscosity at very low shear rates), consistency coefficient, and flow index. Each of these parameters must fall within specific ranges to create a satisfactory thickened fluid for use with dysphagic subjects.

Apparent Viscosity: Apparent viscosity is preferably between about 150 cP to 2000 cP, more preferably between about 200 cP and 2000 cP, and most preferably between about 250 cP and 1800 cP, all measured at about 30 $s^{-1}$. Nectar-type compositions have a preferred apparent viscosity of about 200 to 500 cP, more preferably about 250 cP to about 400 cP, and with a most preferred range of about 300 cP±30 cP (all at 30 $s^{-1}$). (That is, about 270 cP to 330 cP at 30 $s^{-1}$.) Thin honey-type compositions have a preferred apparent viscosity of about 1200 to 1800 cP, more preferably about 1250 cP to about 1700 cP, and with a most preferred range of about 1500 cP (±100 cP) all at 30 $s^{-1}$. (That is, about 1400 cP to about 1600 cP at 30 $s^{-1}$.)

Yield Stress ($\sigma_0$) or Low Shear (1 $s^{-1}$) Viscosity: The data presented in the Examples indicates that yield stress is an important criterion in terms of flow behavior. A higher yield stress requires greater force to initiate flow. Thin honey fluids with yield stress values in excess of about 20 Pa were observed to have a gelled consistency that did not pour. A fluid that does not easily pour influences perception of thickness. More importantly, if a thickened fluid does not flow readily, it will require that the subject tilt his or her head back in order to consume the fluid, which is contraindicated in a dysphagia characterized by incomplete airway closure. Fluids with higher yield stresses also pose difficulty when consumed through a straw because greater intraoral pressure is required to move the liquid through the straw. The ability to generate sufficient intraoral pressure is frequently reduced in dysphagic patients.

Thin honey fluids with yield stress value less than about 10 Pa seem to flow readily. However, fluids with no yield stress are not easily formed into a bolus on the tongue in preparation for swallowing. Thus, thin honey fluids with a low but measurable yield stress (between 5 and 14 Ps at 1 $s^{-1}$) are facilitative for safer swallowing of thickened fluids. For nectar fluids, yield stress is less of a concern because of the lower concentrations of thickeners. Still, a finite value is needed to allow formation of the bolus on the tongue. Yield values between 0 and 2 Pa at 0.1 $s^{-1}$ are appropriate for nectar-thick fluids.

Flow index (n): Flow index (n) is an indication of how a fluid responds at different shear rates. Water is a Newtonian fluid with a flow index of n=1.0, meaning its apparent viscosity does not change with shear rate. Lower n-values indicate more shear thinning behavior: as more force (shear) is applied, the fluid appears thinner, with lower apparent viscosity. Flow index was found to have a significant effect on perceived thickness of thickened fluids. The selection of an ideal target flow index (n) is a key criterion to improving the sensory attributes of thickened fluids. According to the present disclosure, fluids having a flow index falling between about 0.2 to about 0.6, more preferably between about 0.3 and about 0.5 produce lower, more desirable, scores for perceived thickness. Fluids with higher n-values are consistently rated as thicker, less desirable and more mouth-coating. Fluids with lower flow indices (less than 0.2) are highly shear thinning and typically exhibit higher values for yield stress and gel-like structures that are sensorially undesirable and physiologically problematic for dysphagic patients.

Consistency coefficient (k): Of the four rheological parameters that have been defined, only the three listed previously (apparent viscosity, yield stress, and flow index) are independently set. The consistency coefficient is a dependent variable. The k-value of a thickened fluid is automatically determined by the target apparent viscosity required to match a desired endpoint, such as the apparent viscosity of a diagnostic standard.

In short, the present method uses rheological parameters beyond apparent viscosity in order to achieve a beverage that is appropriately designed for therapeutic use, as well as patient enjoyment and appeal. That is, the present method yields compositions that are adequately viscous for use with dysphagic individuals, but are perceived as less thick and more refreshing than conventional thickened liquids that evaluated solely by their apparent viscosity. More appealing thickened fluids for the treatment of dysphagia will result in improved compliance among patients, thus reducing the health-related consequences associated with aspiration due to non-compliance.

It is preferred that the edible solutions comprise a tasty and familiar base liquid vehicle, such as a non-pulpy fruit juice, or a liquid that has been treated to have an identifiable food flavor. Water will also suffice. The vehicle is adjusted to the required apparent viscosity, yield stress, and flow index by adding a suitable thickening agent thereto. See the Examples for a non-limiting list of suitable thickening agents. Any food-grade thickening agent, now known or developed in the future, may be used. Apple juice, for example, is a suitable vehicle. In the case where a contrast agent is included in the formulation, a vehicle having a familiar taste generally yields more useful information regarding the swallowing defects exhibited by the patient because the patient tends to swallow more naturally. This is not the case when a patient is offered a contrast solution that has an offensive taste, odor, or consistency.

The utilities of the subject compositions and methods are several-fold. A primary utility is that by using standardized solutions, consistency in diagnosing and treating dysphagia is promoted. Rather than supplying patients an arbitrarily thickened food or X-ray imaging product, the patient is supplied a solution of known rheological properties. The patient's ability to swallow the solution properly (e.g., without aspiration, retention, regurgitation, and the like) is greatly improved. The subject's condition can also be evaluated consistently over time, either by a gross physical exam or radiographic means or other visualization means, including X-ray, magnetic resonance imaging, and the like. Using two or more standardized solutions as described herein allows the results of two (or more) distinct swallowing studies (e.g., one using the first solution, the other using the second solution) to be compared and contrasted. Moreover, it allows the results from different patients to be compared directly, without variations in the rheological properties of the edible solutions introducing uncontrolled variables into the comparison.

The solutions described herein are useful in radiographic imaging of the mouth because they taste more food-like than conventional barium-containing imaging agents and are therefore more palatable. The rheological properties recited herein for the solutions also promote the proper amount of adhesion between the solutions and the mucus membranes lining the mouth and throat. Consequently, the solutions tend to deposit a sufficient amount of imaging material on the mucus membranes to generate a radiographic image, but do not deposit so much imaging material as to change the swallowing dynamics of the patient under study, nor to leave an artificial coating after swallowing is complete. This is a distinct improvement over conventional barium agents, whose thick, chalky consistency is neither palatable, nor conducive to the generation of good radiographic images of the throat and mouth.

As used herein the term "imaging agent" means any imaging agent, now known or developed in the future, that functions to image the swallowing process or functions to facilitate imaging of the swallowing process. Barium-containing imaging agents are preferred for use with videofluoroscopic imaging of swallowing. Barium sulfate is most commonly used.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations of the present disclosure shall include the corresponding plural characteristic or limitation, and vice-versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention can comprise, consist of, or consist essentially of the essential elements and limitations of the method described and claimed herein, as well as any additional or optional ingredients, components, or limitations described herein or otherwise useful in formulating edible compositions of specifically defined rheological properties.

Liquids may be described by several rheological properties, as discussed above. One of those properties, apparent viscosity, is measured with a viscometer. In simple terms, apparent viscosity is the torque required to rotate a spindle immersed in the solution being analyzed. As discussed in detail by Li et al (1992) *Dysphagia* 7:17-30, viscous liquids are classified as either Newtonian or non-Newtonian. A Newtonian liquid flows at a rate that is directly proportional to the applied shear force while a liquid not obeying this proportionality is deemed to be non-Newtonian.

The complexity and cost of viscometers makes them impractical for dietitians and speech pathologists to utilize in most clinical settings. Therefore, clinicians often resort to simpler means of generating a rough estimate of viscosity, such as the line spread test (LST), as a practical alternative to characterizing the viscosity of thickened liquids.

The LST was originally developed in the 1940's as a simple tool to measure food "consistency." See 8. Grawemeyer & Pfund (1943) *Food Research* 8:105-108, and Adams & Birdsall (1946) *Food Industries* 78-80. The LST measures the "flow of a food/liquid by placing a standard amount of food/liquid in a cylinder, lifting the cylinder and allowing the food/liquid to flow on a horizontal surface for 1 minute and then measuring the distance it has spread. The simplicity of this tool is extremely appealing in clinical practice to measure objectively the general consistency of thickened liquids. As described in the Examples, the LST can roughly distinguish between the viscosity of pre-thickened liquids, and may be a first step toward establishing the utility of this tool in clinical practice.

However, the LST is not overly discriminating as a tool to measure apparent viscosity. Thus, one of the objectives of the methods and compositions described herein is to provide a set or kit of solutions of known and standardized rheological properties, one of which is apparent viscosity.

Viscosity of the compositions is measured at room temperature, generally about 23° C., and can be determined using any number of conventional and commercially available spindle-type viscometers, such as those manufactured by Brookfield Engineering Laboratories, Middleboro, Mass. Brookfield's instruments use a rotating spindle immersed in the fluid to measure viscosity. Brookfield's instruments are of the cone-and-plate rheometer-type design and are ideal for measuring the viscosity of non-Newtonian fluids at low shear rates. The preferred instrument from among Brookfield's offerings is Model LVDV1+, an 18-speed model with digital readout. Viscometers and their operation are widely known and will not be described in great detail herein. For detailed information regarding Brookfield's Model LVDV1+ viscometer, see Brookfield's Manual No. M/92-021-M0101, available from Brookfield. (It is also available on-line at www.brookfieldengineering.com.) For detailed information regarding measuring viscosity, see Li et al, supra, and Brookfield's technical manual entitled "More Solutions to Sticky Problems" (also available at www-.brookfieldengineering.com).

For radiographic imaging of the mouth and throat, it is preferred that compositions having the above-noted rheological properties are formulated using a liquid base vehicle having an identifiable food flavor, such as a juice flavor or honey, chocolate, vanilla, etc. Apple juice is particularly preferred a base vehicle. Apple juice is very advantageous for this purpose because it is widely available, relatively inexpensive, and pulp-free. It is quite palatable and familiar to virtually everyone, and can be stored and transported as a concentrate. The liquid base can be naturally or artificially flavored, and can also contain additional components such as colorants, preservatives, and the like. To the liquid vehicle is added a thickening agent and/or a radio-opaque imaging agent. Because a suspension of radio-opaque material will, by itself, alter the rheological properties of the base solution, depending upon the nature of the suspension used, a thickening agent may not be required to arrive at solutions having the desired rheological characteristics.

Any other type of non-pulpy juice, liquid, or water may be used as the vehicle. A fruit juice is much preferred as the vehicle, however, because of its familiar taste and aroma. An ultimate goal of the method being an accurate evaluation of the patient'[s true swallowing dynamics, presenting an imaging composition which is as closely simulative as possible to a food the patient would normally ingest and enjoy is highly desirable. If the formulation is presented without an imaging agent, the ultimate goal is to provide a satisfying foodstuff that the patient can ingest safely, with a reduced risk of aspirating the formulation or otherwise having the formulation enter the airway rather than the alimentary canal.

If the formulation is to include an imaging agent, the preferred radio-opaque imaging agent is a suspension of barium sulfate. Suitable barium sulfate and barium sulfate suspensions are available commercially from numerous sources. Preferred commercially available barium sulfate and edible suspensions thereof can be obtained from Bracco Diagnostics Inc., Princeton, N.J.

For radiographic imaging purposes, the patient is positioned laterally before a suitable fluoroscopic device and asked to swallow one or more of the three compositions. A videofluoroscope and suitable recording equipment are then used to visualize and record the passage of the composition through the mouth and throat during and after swallowing. If desired, the study can be performed using any combination or both of the two edible solutions.

EXAMPLES

The following examples are submitted to describe in greater detail the methods and compositions described herein. The examples are not intended to limit the scope of the claims in any fashion.

Example 1

Analysis of Thickeners with Dysphagic and Healthy Subjects

Subjects:
Twenty-three (23) healthy patients (22-72 years, mean=40 yr) and fifteen (15) dysphagic control subjects (23-92 years, mean=67 yr) participated in this study, which was approved by the University of Wisconsin Health Sciences Institutional Review Board.

Methods:
1. Videofluoroscopic Oropharyngeal Evaluation: All subjects swallowed two 5 ml trials from a spoon of "VARIBAR"®-brand Nectar, "VARIBAR"®-brand Thin Honey, and each of the six prototype thickened fluids containing 3% barium to make them radiopaque (see Table 3) for a total of 16 swallows. Imaging was completed laterally and pressure data were simultaneously recorded using the Digital Swallowing Workstation. Simultaneous, time-linked oral pressures were measured using the three-sensor array depicted in FIG. 1 and described in detail in Example 2.

Data Reduction:
(a) Residue: Post-swallow barium residue was judged using a three-point scale (0=no residue, 1=coating of residue, 2=pooling of residue) for each swallow at four locations (oral cavity, valleculae, posterior pharyngeal wall, and upper esophageal sphincter).
(b) Timing: Durations of critical swallowing events were assessed via a frame-by-frame analysis of the videofluoroscopic images.
(c) Pressure: Maximum pressure during every swallow was recorded at each sensor location (anterior, middle and posterior). To ensure that the peak pressure was associated with bolus transit the measurement was taken between the time of beginning of posterior bolus movement and when the bolus tail passed into the upper esophageal sphincter.

2. Sensory Assessment: Subjects completed a sensory written evaluation after tasting each prototype fluid using a questionnaire with labeled affective magnitude and visual analog scales assessing overall like/dislike, extent of flavor lingering, amount of mouth-coating and degree of thirst-quenching.

3. Attribute Assessment: Dysphagic subjects also completed an online questionnaire regarding types of thickeners, if any, they had used and their preference for various attributes of thickeners.

Figure 2A:
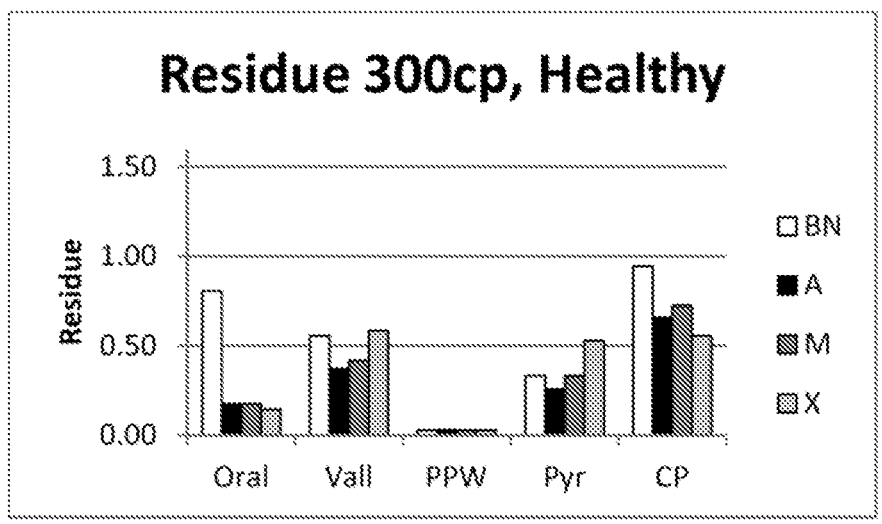
FIG. 2A is a histogram depicting residue data for 300 cP solutions as tested in healthy subjects. For all of FIGS. 2A-2D, Oral=oral cavity, Vall=valleculae, PPW=posterior pharyngeal wall, Pyr=pyriform sinuses, CP= cricopharyngeus, BN=barium nectar, A=agar, M=methylcellulose, X=xanthan gum, BH=barium honey, H=high methoxy pectin, I=iota carrageenan, T=tara gum.
Figure 2B:
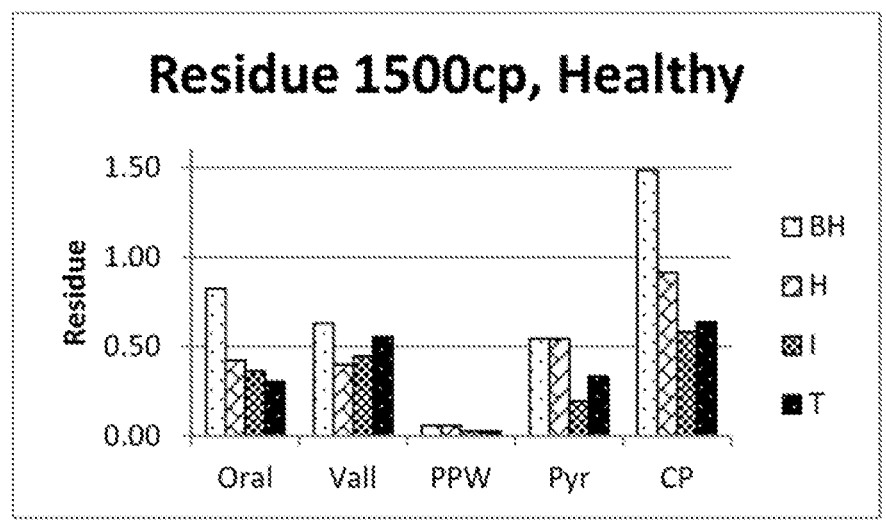
FIG. 2B is a histogram depicting residue data for 1500 cP solutions as tested in healthy subjects.
Figure 2C:
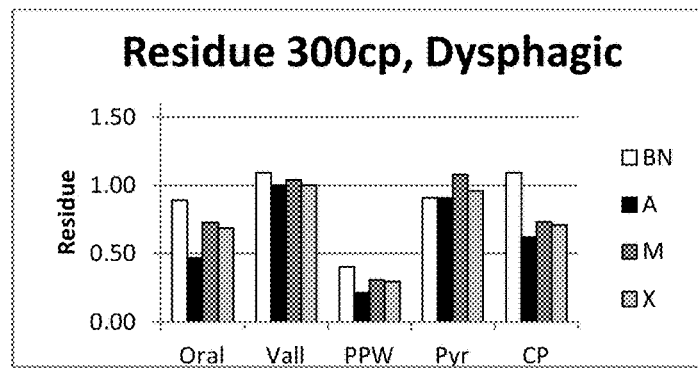
FIG. 2C is a histogram depicting residue data for 300 cP solutions as tested in dysphagic subjects.
Figure 2D:
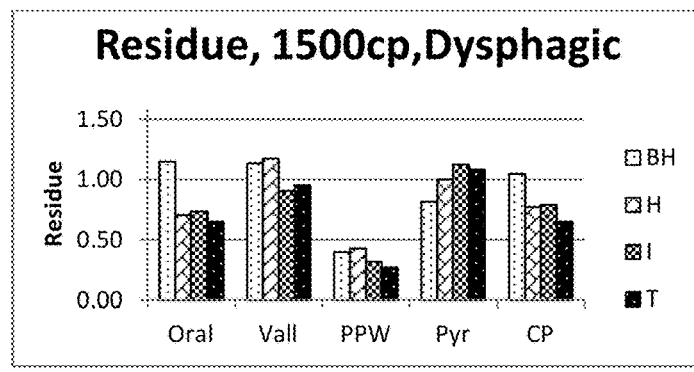
FIG. 2D is a histogram depicting residue data for 1500 cP solutions as tested in dysphagic subjects.

Results:

Residue: Residue data are presented in FIGS. 2A (300 cP, healthy subjects), 2B (1500 cP, healthy subjects), 2C (300 cP, dysphagic subjects), and 2D (1500 cP, dysphagic subjects). Overall, healthy subjects had less residue than dysphagic subjects. For dysphagic subjects within the 300 cP fluids, the least residue in the oral cavity, posterior pharyngeal wall, pyriform sinuses and cricopharyngeus was observed with agar. For dysphagic subjects within the 1500 cP fluids, the least residue in the oral cavity, posterior pharyngeal wall and cricopharyngeus was observed with tara gum. For FIGS. 2A-2D, Oral=oral cavity, Vall=valleculae, PPW=posterior pharyngeal wall, Pyr=pyriform sinuses, CP=cricopharyngeus, BN=barium nectar, A=agar, M=methylcellulose, X=xanthan gum, BH=barium honey, H=high methoxy pectin, I=iota carrageenan, T=tara gum.

Figure 3:
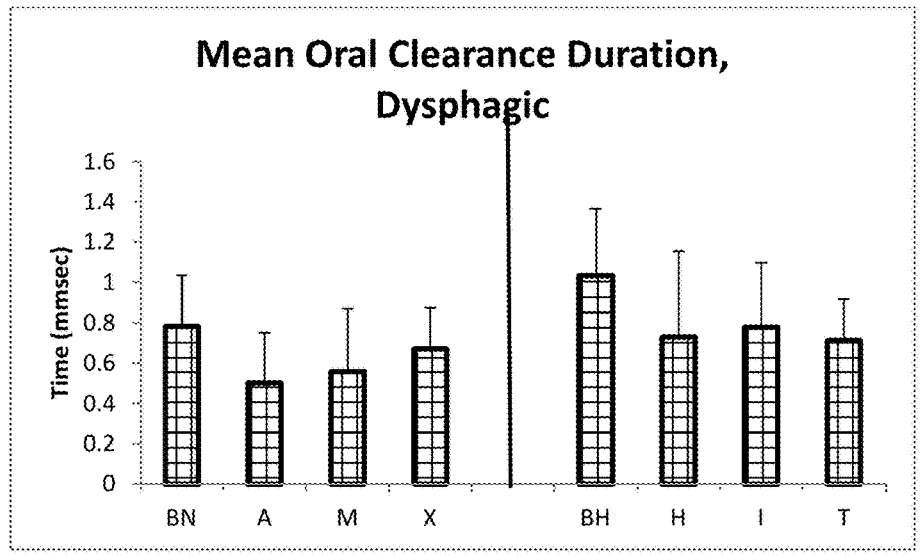
FIG. 3 is a histogram depicting mean oral clearance duration in dysphagic subjects when swallowing 300 cP and 1500 cP solutions.

FIG. 3 is a histogram depicting mean timing of bolus flow through the oral cavity for BN=barium nectar, A=agar, M=methylcellulose, X=xanthan gum, BH=barium honey, H=high methoxyl pectin, I=iota carrageenan, and T=tara gum. As depicted in the figure, bolus clearance in the 300 cPs group of fluids was quickest for agar. In the 1500 cPs group, bolus clearance through the oral cavity was quickest for tara gum.

Figure 4:
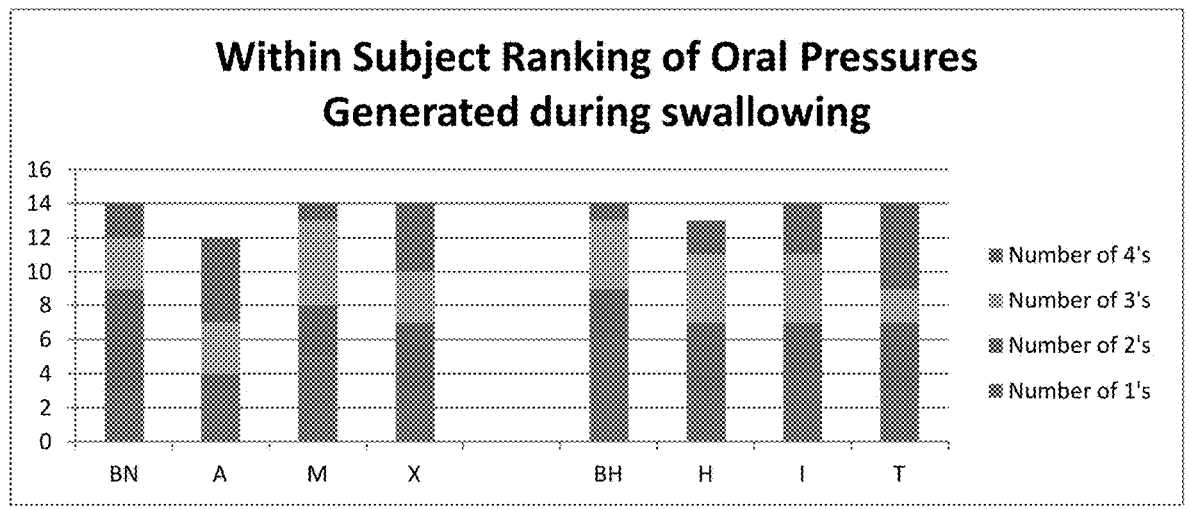
FIG. 4 is a histogram depicting oral pressures generated during swallowing using the pressure array shown in FIG. 1. BN=barium nectar, A=agar, M=methylcellulose, X=xanthan gum, BH=barium honey, H=high methoxy pectin, I=iota carrageenan, T=tara gum.

Maximum pressures generated during swallowing were ranked within subjects for fluids within the same viscosity group (300 cPs and 1500 cPs). The results are shown in FIG. 4. At the anterior sensor within the 300 cPs fluids, dysphagic subjects used the least amount of pressure more often with agar (300 cPs group) and tara gum (1500 cPs group) compared to other fluids within the same group. As shown in FIG. 4, pressures generated during swallowing are presented as a ranking within subject. A score of "1" indicates that a subject generated the most pressures for that liquid compared to the other three liquids in that viscosity group. A score of "4" indicates that a subject generated the least amount of pressure for a liquid compared to the others in that group. The count of each scores are presented in each bar of the histogram. Missing data were due to sensor failure. Abbreviations are as given previously.

Figure 5:
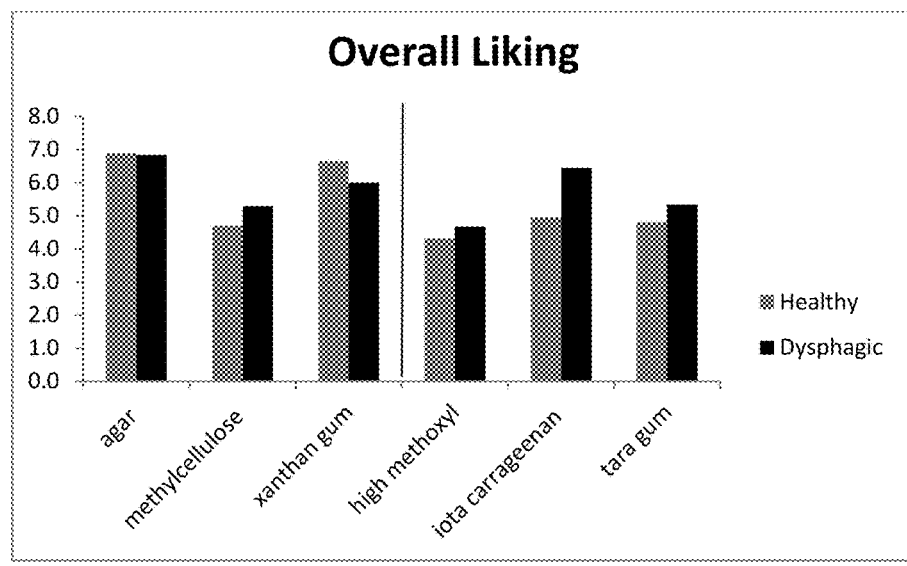
FIG. 5 is a histogram depicting overall liking of 300 and 1500 cP solutions in both healthy and dysphagic subjects.
Figure 6:
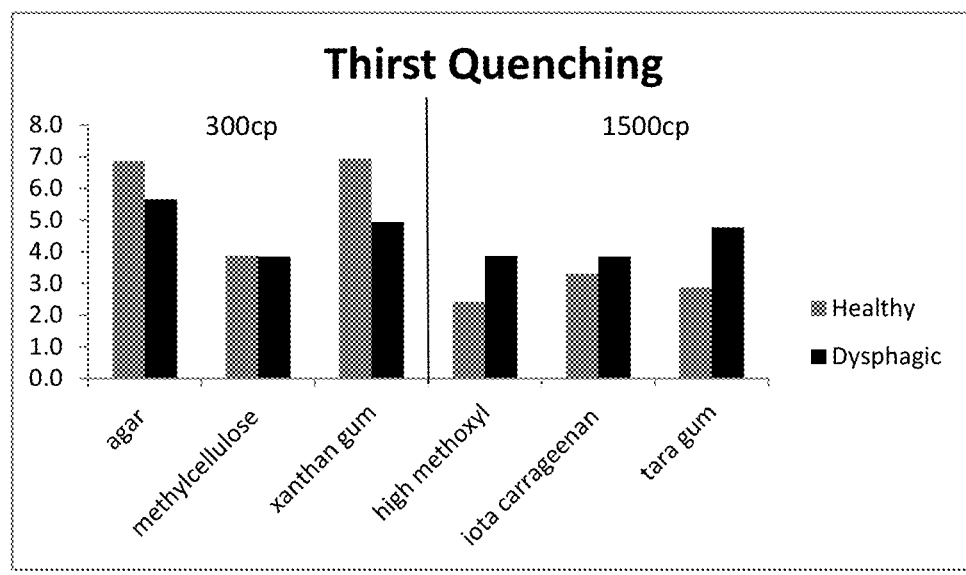
FIG. 6 is a histogram depicting thirst quenching of 300 and 1500 cP solutions in both healthy and dysphagic subjects.

Sensory:

Dysphagic and healthy subjects rated agar highest in "Overall Liking" compared to other 300 cP fluids. See FIG. 5. Within the 1500 cP fluids, iota carrageenan was preferred by dysphagic subjects and healthy subjects equally preferred iota carrageenan and tara gum. Agar and tara gum were rated as most thirst quenching by the dysphagic subjects. See FIG. 6.

Attributes:

Dysphagic subjects were provided a list of 35 potential attributes and asked which ones they would prefer to have in thickened liquids they purchase. The attributes ranked as most preferred were high protein, thirst quenching, high fiber, clear (non-milky), low sweet and chocolate flavored.

Conclusions:

Overall, the fluids most similar rheologically to the barium standards (agar in the 300 cP group and tara gum in the 1500 cP group) were observed to result in the least amount of post-swallow residue, meaning that patients would be less at risk for aspirating the fluid after the swallow. Additionally, agar and tara gum required the lowest lingual pressures to move the bolus through the oral cavity and were cleared faster from the oral cavity indicating that weaker, more disabled patients would be able to swallow these beverages more safely than the other thickened fluids. When patients were questioned about their preferences, agar was rated highest in "overall liking" and both agar and tara gum were rated highest in thirst quenching-both of which are critical characteristics for compliance with drinking thickened liquids.

Example 2

Assessing Thickened Beverages Using a Variety of Thickeners

Samples:

The 15 thickeners listed below in Table 1 were used to prepare 30 thickened beverage samples at nectar and thin honey viscosities. These beverages were formulated to match the viscosities of "VARIBAR"®-brand diagnostic fluids: $\eta_{30\,s-1}$=300±30 cP for nectars and $\eta_{30\,s-1}$=1500±100 cP for thin honeys. (In the records of the U.S. Patent & Trademark Office, "VARIBAR" is a recorded as registered trademark of E-Z-EM, Inc., Lake Success, N.Y., USA. However, E-Z-EM was acquired by Bracco Diagnostics Inc. in April of 2008.) Individual samples of 28 ml were removed from the refrigerator an hour before serving and served at room temperature in 60 ml cups labeled with random, 3-digit codes. New codes were generated for each test session.

All beverage samples were prepared using a water-based "base liquid". The base liquid was sweetened with 3% (w/w) sucrose, and pH was adjusted to 4.45±0.03, using citric acid (Tate & Lyle, Decatur, Ill., USA) and buffered with sodium citrate (Tate & Lyle). Prepared samples were flavored using lemonade-type flavor 645081 (Guividan Flavors Corp., Cincinnati, Ohio), at a rate of 0.24% (w/w).

Thickeners were mixed into base liquid using a rotational mixer (Controller: Master Servodyne Controller, Cole Palmer Instrument Co., Chicago, Ill., USA; Rotational head: Model E650, 1/16-3/8 in CAP, 3/8-24 THD, Robbins Meyers Electro-Craft, Hopkins, Minn., USA) equipped with a 12×5/16 in diameter stainless steel impeller shaft (Model A712, Caframo, Wiarton, ON, Canada) and a 1.5 in stainless steel blade (Caframo).

Rheological Profiling:

Apparent viscosity of fluid samples at 30 s$^{-1}$ was initially determined using Brookfield DVIII-Ultra Programmable Rheometers (Brookfield Engineering, Middelboro, Mass., USA), models HA and RV, with a concentric cylinder configuration. All experiments were conducted under isothermal conditions at 22.0±0.1° C. A stepped shear rate test (ascending and descending) was used, ranging from 3.75 s$^{-1}$ to 60 s$^{-1}$ and allowing for ten revolutions at each step. The shear rate and shear stress data were determined by Rheocalc-brand software (Brookfield Engineering).

Further rheological profiling was performed on the same samples using a Universal Dynamic Spectrometer (Paar Physica UDS 200 Controlled Stress Rheometer, Physica Messtechnik GmbH, Stuttgart, Germany). Flow curves were determined using logarithmically stepped shear rates from 1000 s$^{-1}$ to 1 s$^{-1}$. Apparent viscosity (30 s$^{-1}$, 22° C.), flow index (n), consistency coefficient (K), and yield stress ($\sigma_0$) were measured for all beverage samples. Data were recorded and fit to mathematical models using Physica RheoPlus-brand software (Physica Messtechnik). Yield point values for the fluids were determined by the stress required to initiate flow at constant shear. One shear rate did not work well for both nectar and thin honey consistencies, so different shear rates were used for each; for nectars, $\gamma=0.1$ s$^{-1}$, and for thin honeys, $\gamma=1.0$ s$^{-1}$.

Subjects:

Twenty-four subjects (6 males, 18 females) aged 19- 58 with a median age of 26, were recruited from the University of Minnesota using an email screener. Subjects having a swallowing disorder and/or any food allergies were excluded. Subjects were paid a cash incentive for their participation. The University of Minnesota Institutional Review Board approved this study.

TABLE 2

Thickened Beverage Texture Lexicon

| Attribute | Description |
|---|---|
| Thickness | The force required to push the liquid against the roof of the mouth. |
| Adhesiveness | The amount of work needed to remove the liquid from the palate. |
| Stickiness | The amount of force needed to pull the tongue away from the roof of the mouth. Touch the tongue to the roof of the mouth, then pull it directly down. |
| Slipperiness | The enhanced lubricating or friction-reducing qualities at the back of the throat as you swallow |
| Mouth-coating | The degree to which the product coats the inside of the mouth after swallowing |

During the training session, each panelist was provided with a subset of ten different thickened beverages chosen as they best represented the entire set of 30 beverages in terms of thickness and mouth-coating, and included all chemical categories of thickeners. The different sensory attributes were illustrated by selecting samples from this set that varied perceivably in each sensory attribute. Panelists were asked to plug their noses using nose clips while rating tastes

TABLE 1

Thickeners Used for Beverages

| Thickener | Trade Name | Supplier | Consistency | Usage Level (% w/w) |
|---|---|---|---|---|
| Agar | Quick Gelagar - QT30 | Setexam (Kenitra, Morocco) | Thin Honey<br>Nectar | 0.87<br>1.72 |
| Sodium alginate | Satialgine ™ S 1100 | Cargill (Minnetonka, MN) | Thin Honey<br>Nectar | 1<br>1.7 |
| Iota (ι) carrageenan | Viscarin ® SD 389 | FMC BioPolymer (Philadelphia, PA) | Thin Honey<br>Nectar | 1.09<br>1.77 |
| Cellulose gum | TIC Pretested ® Ticaloid ® EZ-1900 Powder | TIC Gums (White Marsh, MD) | Thin Honey<br>Nectar | 2.93<br>5.36 |
| Methylcellulose | Ticacel ® LV Powder | TIC Gums | Thin Honey<br>Nectar | 1.84<br>2.94 |
| Microcrystalline cellulose | Avicel ® AC 4125 | FMC BioPolymer | Thin Honey<br>Nectar | 4.78<br>6.59 |
| Guar gum | Guar Gum FG6070 | P.L. Thomas & Co., Inc. (Morristown, NJ) | Thin Honey<br>Nectar | 0.56<br>1.04 |
| Konjac gum | Ticagel ® Konjac HV | TIC Gums | Thin Honey<br>Nectar | 0.32<br>0.59 |
| Tara gum | TIC Pretested ® Tara Gum 100 | TIC Gums | Thin Honey<br>Nectar | 0.55<br>0.97 |
| Xanthan gum | Ticaxan ® Rapid-3 Powder | TIC Gums | Thin Honey<br>Nectar | 0.53<br>2.16 |
| Calcium caseinate | Ca. caseinate Spray | DMV International (Veghel, Netherlands) | Thin Honey<br>Nectar | 11.51<br>13.1 |
| High methoxyl pectin | Unipectine ™ AYD 258 | Cargill | Thin Honey<br>Nectar | 3.25<br>4.96 |
| Low methoxyl pectin | Coyote Brand Pectin LM 0929 | Gum Technology Corporation (Tucson, AZ) | Thin Honey<br>Nectar | 6.35<br>9.77 |
| Waxy rice starch | Remyline XS-B - Extra stable waxy rice starch | A&B Ingredients, Inc. (Fairfield, NJ) | Thin Honey<br>Nectar | 3.61<br>5.26 |
| Acetylated distarch phosphate | Stabitex - Instant ™ 12625 | Cargill | Thin Honey<br>Nectar | 4.33<br>5.43 |

Training Session:

Panelists attended one training session during the first week of the study. At the beginning of the session, they were provided with a lexicon based on the texture lexicon described by Hootman (1992). The lexicon was modified using panelist input to describe relevant differences among the 30 products sampled (Table 2).

in order to avoid aromas. The remaining sensory attributes were rated without nose clips. All flavors besides lemon flavor were grouped together and rated on an intensity scale as "Other Flavor." Panelists were also instructed how to rate the different textural attributes: thickness, adhesiveness, stickiness, slipperiness and mouth-coating (Table 2).

The panelists also learned a standardized sampling method to minimize variability in delivery as well as perception of the sensory attributes. The standardized sampling method ensured that each panelist evaluated the same amount of each sample. The standardized method required that they first gently stir the sample 30 times with a plastic spoon (Bakers and Chefs™ Plastic Spoons, Bentonville, Ark., USA) in order to mimic the stirring done before instrumental measurements were taken. Panelists were prompted to do this for each beverage during the training and test sessions by computerized instructions. Panelists then had to fill the spoon full with the sample, level it off if necessary with a plastic coffee stirrer (Propak™ Coffee/Bar Stirrers), place the nose clips on, put the spoonful of sample in their mouth and evaluate the sample for sweet, sour and bitter taste, remove the nose clips and evaluate the sample for lemon and other flavor. (These attributes were rated by the panelists to prevent them from placing these sensations into ratings of the texture attributes.) Panelists were allowed to expectorate this first spoonful of sample after evaluating it. Then, they had to consume a second spoonful of the same sample and evaluate thickness, adhesiveness, stickiness and slipperiness before swallowing. Mouth-coating and number of swallows required to cleanse the palate were evaluated after the second spoonful was swallowed.

Data Collection Sessions:

The seven data collection sessions were divided into four sensory evaluation sessions, one lingual pressure measurement session and two residual mouth-coating measurement sessions.

Sensory Evaluation Sessions:

Panelists typically attended four sensory evaluation sessions during two consecutive weeks. The set of 30 thickened beverages was randomly divided into two groups of 15 beverages. The same 15 beverages were served to all panelists at each session. The position in which each of these 15 beverages was served at each session was determined by a design for 15 treatments in two blocks balanced for the effect of order of presentation and first-order carry-over effects (MacFie et al., 1989). Panelists sampled the complete set of 30 beverages in the first week (i.e. 15 beverages during session 1 and the remaining 15 during session 2). Similarly, all 30 beverages were sampled again through the second week.

The panelists tasted each beverage using the standardized sampling method described in the training session. At each session, the panelists rated each beverage for taste—sweet, sour and bitter; flavor—lemon and other; and texture— thickness, adhesiveness, stickiness, slipperiness, mouth-coating, and the number of swallows required to clear the palate. Ratings for all these sensory attributes were collected on a 15-point numerical category scale, with end-points of 0 and 15. The scale had tick marks labeled with numbers at regular intervals of 1 unit. Panelists could choose any point on the scale from 0 to 15, with end anchors "none" and "intense." Panelists also noted the number of swallows required to cleanse the palate after the thickened beverage was swallowed. The first swallow was not included in this rating. Twenty-two (22) panelists completed all four sensory evaluation sessions.

Lingual Pressure Measurement Session:

Panelists attended one swallowing pressure measurement session. A three-sensor array was affixed to the hard palate using Stomahesive™-brand adhesive (ConvaTec, Skillman, N.J., USA) with the anterior sensor at the alveolar ridge and the posterior sensor at the approximate junction of the hard and soft palates. See FIG. 1, which is a photograph of the sensor array positioned within the mouth. This array was connected to a Digital Swallowing Workstation (KayPENTAX, Montvale, N.J., USA) that recorded the pressure (mm Hg) exerted by the tongue on each sensor as the panelist swallowed samples. The panelists were provided a leveled spoonful of each of the complete set of 30 thickened beverages and asked to swallow the sample in a single swallow. The order in which each panelist was served these 30 beverages was determined by a 30×30 Latin square design balanced for order and carry-over effects, generated using DesignExpress®-brand software (Product Perceptions Ltd., Horley, Surrey, UK). Twenty-two (22) panelists attended the session, but useful data could not be collected from two panelists due to discomfort caused by the lingual pressure array.

Residual Mouth-Coating Measurement Session:

Panelists attended two, hour-long residual mouth-coating measurement sessions during two consecutive weeks. Riboflavin (1 g/L; Sigma-Aldrich Co., St. Louis, Mo.) was incorporated into the base liquid of all the thickened beverages during preparation. The complete set of 30 thickened beverages was randomly divided into two groups of 15 beverages. At each session, all panelists were served the same set of 15 thickened beverages. The positions in which these 15 beverages were served was determined by a design for 15 treatments in two balanced blocks of 30 consumers each so as to balance the effect of order of presentation and first-order carry-over effects (MacFie et al., 1989).

A rinse-and-spit protocol was developed using the following steps: panelists gently stirred the sample 30 times with a plastic spoon (Bakers and Chefs™ Plastic Spoons, Bentonville, Ark.), filled the spoon full with the sample, leveled it off if necessary with a plastic coffee stirrer (Propak™ Coffee/Bar Stirrers), and swallowed this spoonful. Panelists then rinsed their mouth with 10 ml of water, swishing it three times inside the mouth, and spit this rinse water into a 16 oz spit cup (Dart® Foam Cups, Mason, Mich., USA) labeled with the same code number as the sample. This rinse-and-spit protocol was repeated five times after swallowing each sample. (At the start of each session, panelists swallowed a spoonful of water instead of the thickened beverage sample, to familiarize them with the protocol as well as to remove food particles from their mouth.)

The riboflavin concentration in the rinse water from each judge for each sample was determined using a chemical analysis and fluorescent spectroscopy method (Scott et al, 1946). The total riboflavin content in the rinse water was calculated by multiplying this riboflavin concentration by the volume of rinse water. We considered the total riboflavin content to be a measure of residual mouth-coating.

Data Analysis:

Raw data from the tests above were compiled on Microsoft Excel-brand sheets. Statistical analyses were carried out using SAS computer software (The SAS System for Windows™, Version 9.2, The SAS Institute Inc., Cary, N.C., USA) and XLSTAT™ 2010 (Addinsoft SARL, New York, N.Y., USA). Unless otherwise noted, statistical significance was set at 0.05. Although the taste and flavor measurements varied among the beverages, they were unrelated to any of the rheological, sensory texture or swallowing pressure measurements and are not included in any data analyses reported here.

Linear regression fit by restricted maximum likelihood (REML) was used to relate sensory and swallowing pressure measurements to the rheological measurements. Similar analyses were run separately for thin honey beverages and nectar beverages in order to visualize relationships within each of the two viscosity ranges.

Principal components analysis with varimax rotation (XLSTAT) was used to summarize the relationships among the three groups of measurements (sensory, rheological and swallowing pressure) for the nectar and the thin honey beverages separately. The main data set for each principal components analysis contained the 15 beverages as observations and the rheological measurements as variables. Sensory texture measurements and swallowing pressures for each of the 15 beverages were added as supplementary variables.

The relationship between the sensory perception of mouth-coating and instrumental measurement for predicting mouth-coating was examined using linear regression. The dependent variable was the sensory perception of mouth-coating; the instrumental measurement of residual riboflavin served as a predictor. Each judge was included in the model as a dummy variable.

Selection of Thickeners to be Used in Videofluoroscopy:

Six thickeners were chosen from the fifteen thickeners initially selected for formulation to move forward to videofluoroscopy studies. Three different thickeners were used to produce fluids at Nectar consistency and three others at Thin Honey consistency. See Table 3. Thickener selection for two of the fluids was based on rheological similarities (apparent viscosity, flow index, and consistency) to the diagnostic fluids ("VARIBAR"®-brand Nectar and Thin Honey). The remaining four thickeners were selected based on sensory attributes. Those thickeners that were rated at the furthest sensory extremes (i.e., minimum or maximum thickness, mouth coating, adhesiveness, slipperiness) were chosen for Nectar or Thin Honey consistency. The thickeners selected for Nectars were xanthan gum, methylcellulose gum, and agar. For Thin Honeys, the thickeners selected were high methoxyl pectin, iota carrageenan, and tara gum.

ties, thus shifting the focus towards relationships of the other rheological properties with the sensory and swallowing measurements.

Figure 7:
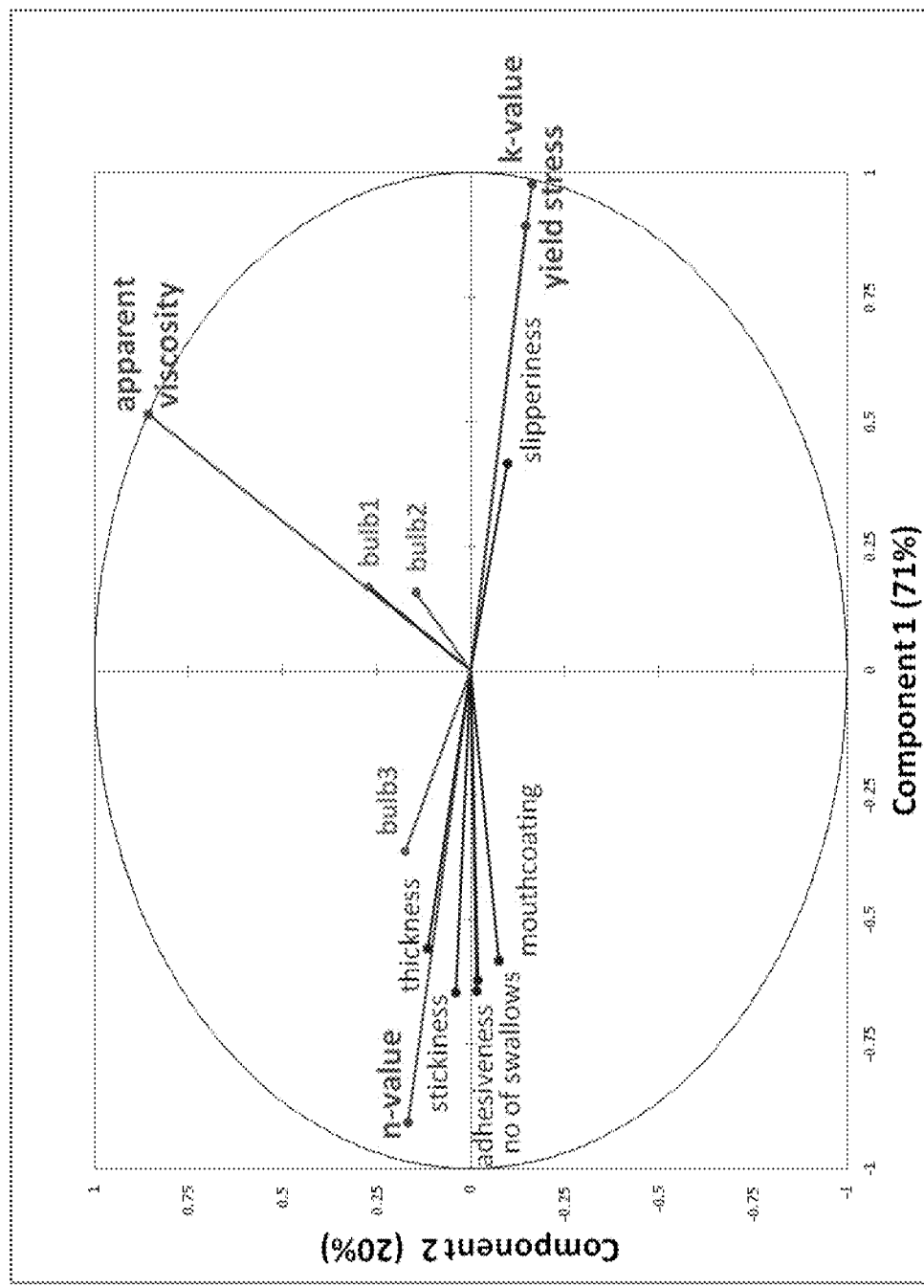
FIG. 7 is a principal components plot showing relationships among rheological, sensory, and swallowing measurements for nectar beverages.

Nectar Beverages:

The sensory properties thickness, stickiness, adhesiveness, mouth-coating and number of swallows were highly negatively correlated with principal component 1, and highly positively correlated with the flow behavior index (n-value). See FIG. 7 and Table 3. FIG. 7 is a principal components plot showing relationships among rheological, sensory and swallowing pressure measurements for nectar beverages. The first component (horizontal axis) is highly positively correlated with k-value (consistency coefficient) and highly negatively correlated with n-value (flow behavior index). The second component is strongly positively correlated with apparent viscosity. As shown in FIG. 7, slipperiness was negatively correlated with n-value and with all the other sensory texture attributes. Principal component 2 and apparent viscosity were not significantly correlated with any of the sensory or swallowing pressure measurements. Although bulb 1 and bulb 2 pressures were significantly correlated with each other (both appearing in the upper-right quadrant of FIG. 7), they were not significantly related to any of the principal components, or to any rheological measurements.

Figure 8:
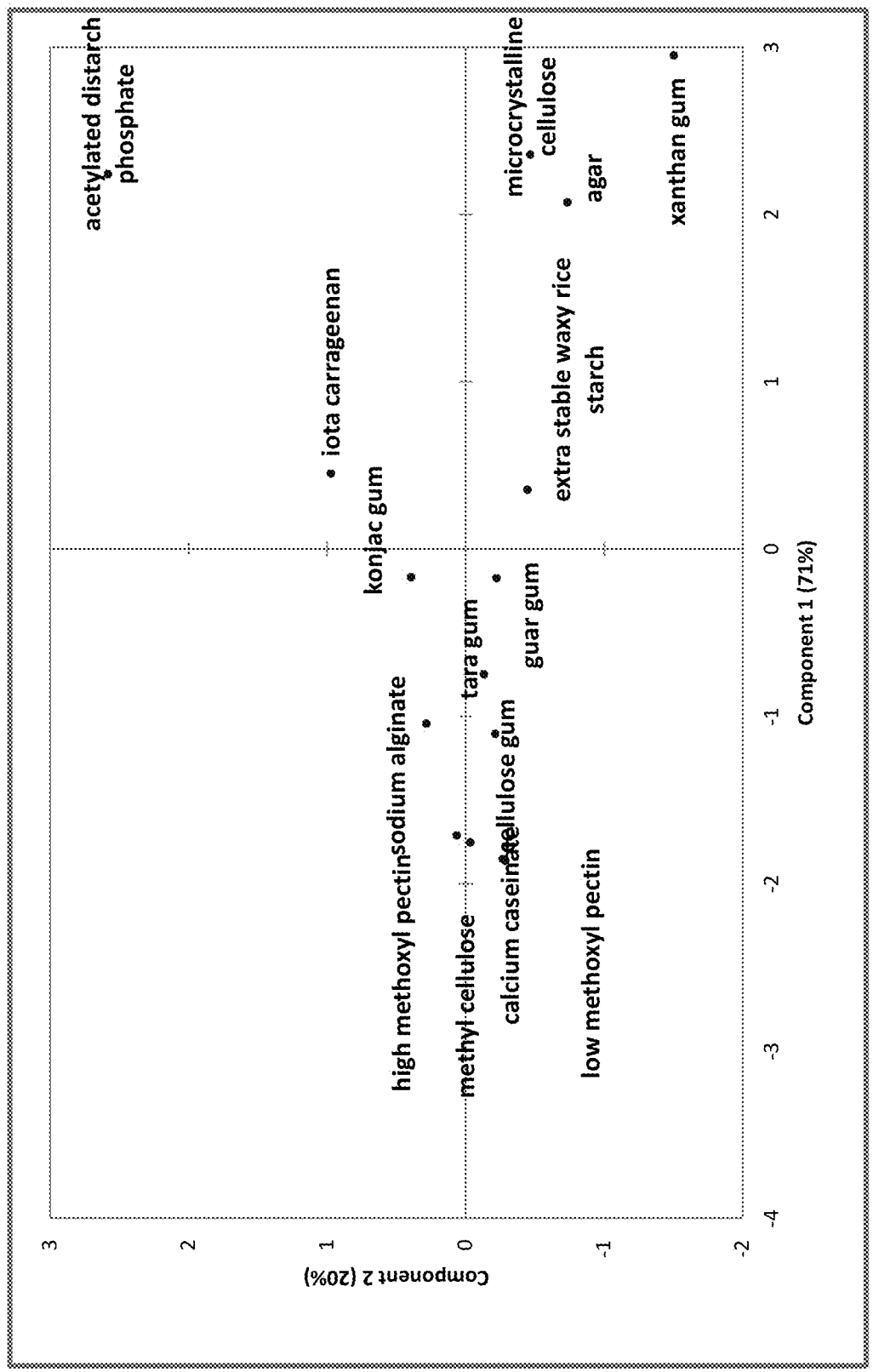
FIG. 8 is a principal components plot for nectar beverages showing the factor scores for the 15 thickeners used in the Examples.

FIG. 8 is a principal components plot for nectar beverages showing the factor scores for the 15 thickeners. The first component (horizontal axis) is highly positively correlated with k-value (consistency coefficient) and highly negatively correlated with n-value (flow behavior index). The second component is strongly positively correlated with apparent viscosity. As shown by the data in FIG. 8, the sensory attributes thickness, adhesiveness, stickiness, mouth-coating, and number of swallows were highly correlated with

TABLE 3

Rheology of Thickeners Selected for Videofluoroscopic and Sensory Analysis

| Thickened Fluid | Apparent Viscosity ($\eta_{30s-1}$), cP | Flow Index (n) | Consistency (K) | Yield Stress ($\sigma_0$), Pa · s |
|---|---|---|---|---|
| Diagnostic Standards | | | | |
| "VARIBAR" Thin Honey | 1440 | 0.53 | 8104 | 10250 |
| "VARIBAR" Nectar | 231 | 0.34 | 2468 | 1510 |
| Rheology-based Choices | | | | |
| Tara Gum Thin Honey | 1413 | 0.38 | 9970 | 6918 |
| Tara Gum Thin Honey + 3% Barium | 1405 | 0.38 | 9879 | 7210 |
| Agar Nectar | 282 | 0.33 | 2898 | 2410 |
| Agar Nectar + 3% Barium | 287 | 0.3236 | 3145 | 2225 |
| Sensory- based choices | | | | |
| HM Pectin Thin Honey | 1498 | 0.74 | 3125 | 2295 |
| HM Pectin Thin Honey + 3% Barium | 1470 | 0.74 | 3048 | 2530 |
| ι-CRG Thin Honey | 1248 | 0.28 | 15168 | 35925 |
| ι-CRG Thin Honey + 3% Barium | 1395 | 0.25 | 18710 | 35400 |
| Xanthan Gum Nectar | 247 | 0.22 | 3756 | 2853 |
| Xanthan Gum Nectar + 3% Barium | 242 | 0.20 | 4020 | 3045 |
| Methylcellulose Nectar | 263 | 0.56 | 343 | 38 |
| Methylcellulose Nectar + 3% Barium | 276 | 0.59 | 361 | 44 |

Results:

The relatively huge differences in viscosity between the two thickness levels (nectar and thin honey) overwhelmed comparisons among the thickeners, so the observations were separated into those for the nectar beverages and those for the thin honey beverages. The object was for the beverages within these subsets to have very similar apparent viscosities, thus shifting the focus towards relationships of the other each other (all $r>0.95$; computed across means of the 15 nectar beverages). The n-value was positively correlated with all these sensory attributes ($0.77<r<0.92$); the k-value was negatively correlated with all these sensory attributes ($-0.63<r<-0.54$). None of the rheological measurements were significantly related to the swallowing pressure measurements ($-0.42<r<0.33$). See Table 3.

TABLE 3

Best linear regression equations, fit by restricted maximum likelihood (REML), relating sensory and swallowing pressure measurements to the rheological measurements for nectar fluids only. Values are beta coefficients (the change in the sensory or swallowing pressure measurement produced by a one unit increase in the rheological measurement.) Empty cells indicate no significant relationship between the sensory or swallowing pressure measurement and the rheological measurement.

| Sensory/ Swallowing Attribute | Intercept | Apparent viscosity | n-value | k-value | Adjusted R² |
|---|---|---|---|---|---|
| Thickness | −2.6 | | 7.6 | 0.00084 | 0.86 |
| Adhesiveness | −4.7 | | 10.2 | 0.0001 | 0.80 |
| Stickiness | −2.2 | | 6.3 | 0.00051 | 0.69 |
| Slipperiness | 13.8 | | −9.7 | −0.0012 | 0.74 |
| Mouth coating | −3.6 | | 11.8 | 0.0013 | 0.72 |
| No. of swallows | −1.15 | | 5.48 | 0.00056 | 0.80 |
| Bulb 1 | 154 | | | | |
| Bulb 2 | 154 | | | | |
| Bulb 3 | 170 | | | | |

Figure 9:
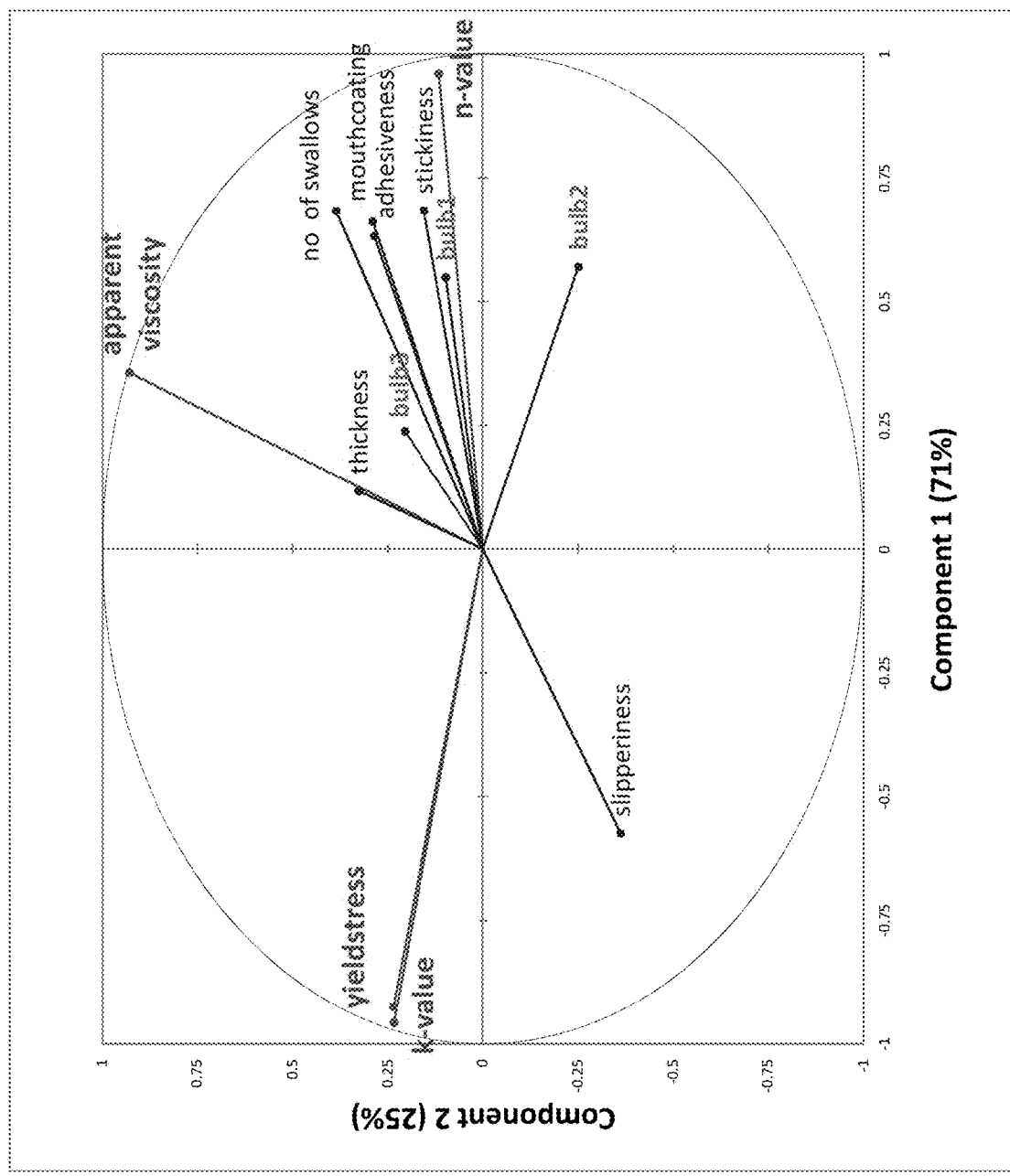
FIG. 9 is a principal components plot showing relationships among rheological, sensory, and swallowing measurements for thin honey beverages.

Thin Honey Beverages:

The sensory properties adhesiveness, stickiness, mouth-coating and number of swallows were positively correlated (r>0.6) with component 1 and with the n-value. See FIG. 9 and Table 4. Slipperiness was negatively correlated with component 1, with the n-value and with all the other sensory texture attributes. Bulb 1 and bulb 2 pressures were significantly correlated with each other and had correlations of 0.55 and 0.57 respectively with principal component 1. Both bulb 1 and bulb 2 pressures were negatively correlated to yield stress and to k-value, and were positively correlated to n-value. Bulb 3 pressure was negatively correlated to slipperiness. FIG. 9 is a principal components plot showing relationships among rheological, sensory and swallowing pressure measurements for thin honey beverages. The first component (horizontal axis) is highly positively correlated with n-value (flow behavior index) and highly negatively correlated with k-value (consistency co-efficient) and yield stress. The second component is strongly positively correlated with apparent viscosity. The sensory attributes adhesiveness, stickiness, mouth-coating, and number of swallows were highly correlated with each other (all r>0.93; computed across means of the 15 thin honey beverages). The n-value was positively correlated with all these sensory attributes (0.74<r<0.76); the k-value was negatively correlated with all these sensory attributes (−0.6<r<−0.52). Bulb 2 pressure was positively related to the n-value (r=0.52), negatively related to the k-value (r=−0.64), and negatively related to yield stress (r=−0.55). Bulb 1 pressures were negatively related to yield stress; bulb 3 pressures were not significantly correlated with any of the rheological measurements. See Table 4.

Figure 10:
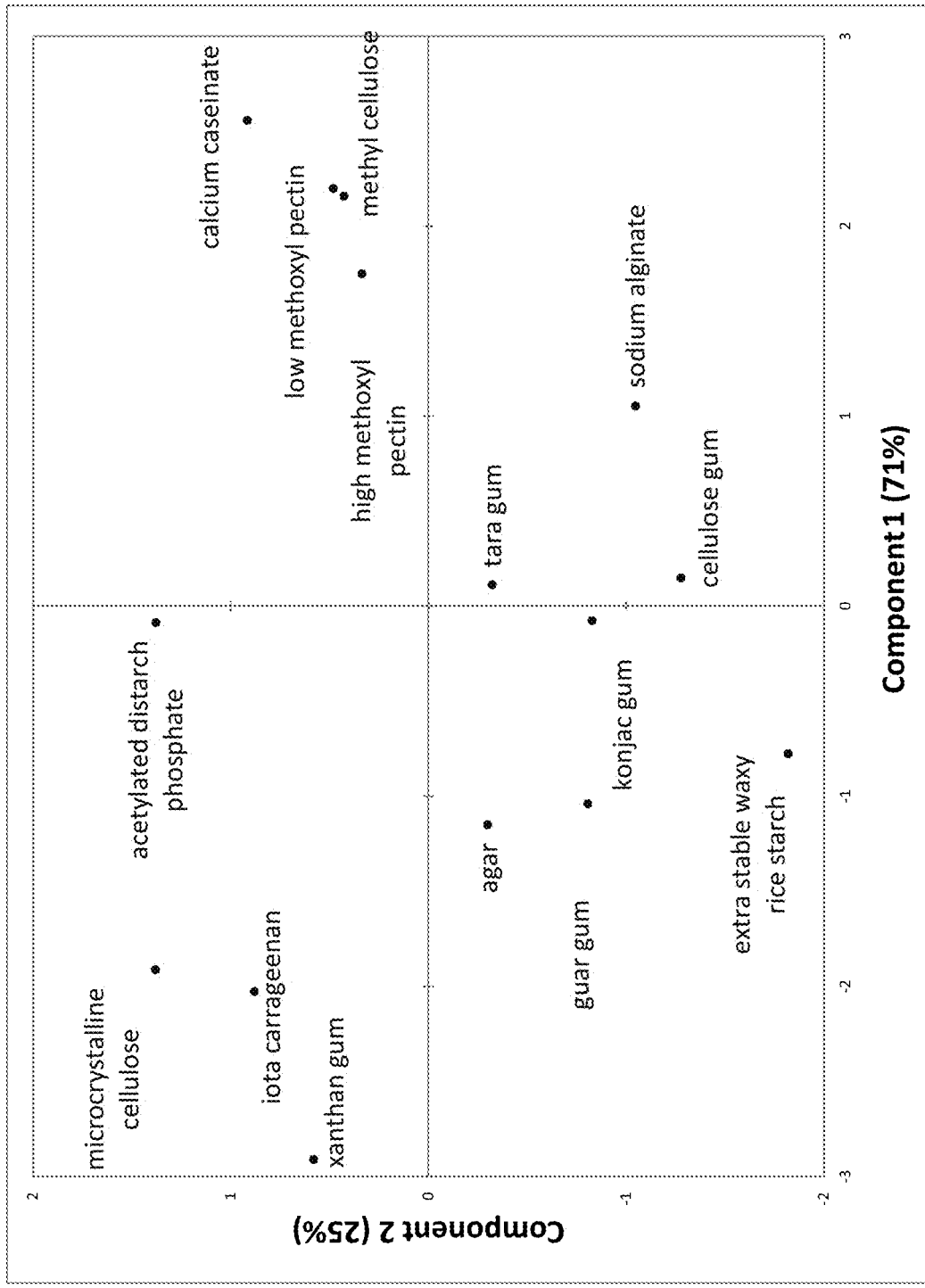
FIG. 10 is a principal components plot for thin honey beverages showing the factor scores for the 15 thickeners used in the Examples.

FIG. 10 is a principal components plot for thin honey beverages showing the factor scores for the 15 thickeners. The first component (horizontal axis) is highly positively correlated with n-value (flow behavior index) and highly negatively correlated with k-value (consistency co-efficient) and yield stress. The second component is strongly positively correlated with apparent viscosity.

TABLE 4

Best linear regression equations, fit by restricted maximum likelihood (REML), relating sensory and swallowing pressure measurements to the rheological measurements for thin honey fluids only. Values are beta coefficients (the change in the sensory or swallowing pressure measurement produced by a one unit increase in the rheological measurement.) Empty cells indicate no significant relationship between the sensory or swallowing pressure measurement and the rheological measurement.

| Sensory/ Swallowing Attribute | Intercept | Apparent viscosity | n-value | k-value | Yield stress | Adjusted R² |
|---|---|---|---|---|---|---|
| Thickness | 3.8 | | 5.8 | | 0.082 | 0.34 |
| Adhesiveness | −1.7 | | 12 | | | 0.6 |
| Stickiness | 2.1 | | 6.2 | | | 0.54 |
| Slipperiness | 5.4 | | −2.5 | | | 0.34 |
| Mouth coating | 2.4 | | 7.9 | | | 0.53 |
| No. of swallows | 2.6 | | 3.6 | | | 0.54 |
| Bulb 1 | 177 | | | | −0.65 | 0.25 |
| Bulb 2 | 176 | | | −0.001 | | 0.36 |
| Bulb 3 | 188 | | | | | |

Sensory Attributes and Swallowing Pressures:

Relationships between the swallowing pressures and the sensory attributes were generally weak, and even in the cases of significance, linear relationships had low R² values. Swallowing pressures for nectar beverages were negatively related to the number of swallows and positively related to thickness. See Table 5. Swallowing pressures for thin honey beverages were not consistent among the three bulbs. See Table 6.

TABLE 5

Best linear regression equations, fit by restricted maximum likelihood (REML), relating swallowing pressures and sensory attributes. Data for nectar thick samples

| Swallowing pressure | Intercept | Thick | Adhesive | Sticky | Slippery | Mouth coating | No. of swallows | Adjusted R² |
|---|---|---|---|---|---|---|---|---|
| Bulb 1 | 146 | 13.7 | | | | | −11.3 | 0.02 |
| Bulb 2 | 181 | | | | | | −9.8 | 0.02 |
| Bulb 3 | 163 | 9.5 | −7.3 | | | | | 0.01 |

TABLE 6

Best linear regression equations, fit by restricted maximum likelihood (REML), relating swallowing pressures and sensory attributes. Data for thin honey samples

| Swallowing pressure | Intercept | Thick | Adhesive | Sticky | Slippery | Mouth-coating | No. of swallows | Adjusted $R^2$ |
|---|---|---|---|---|---|---|---|---|
| Bulb 1 | 133 | | | | | | 8.0 | 0.19 |
| Bulb 2 | 161 | | −12 | 15.8 | | | | 0.16 |
| Bulb 3 | 183 | | | −7.7 | | 7.1 | | 0.30 |

Figure 11:
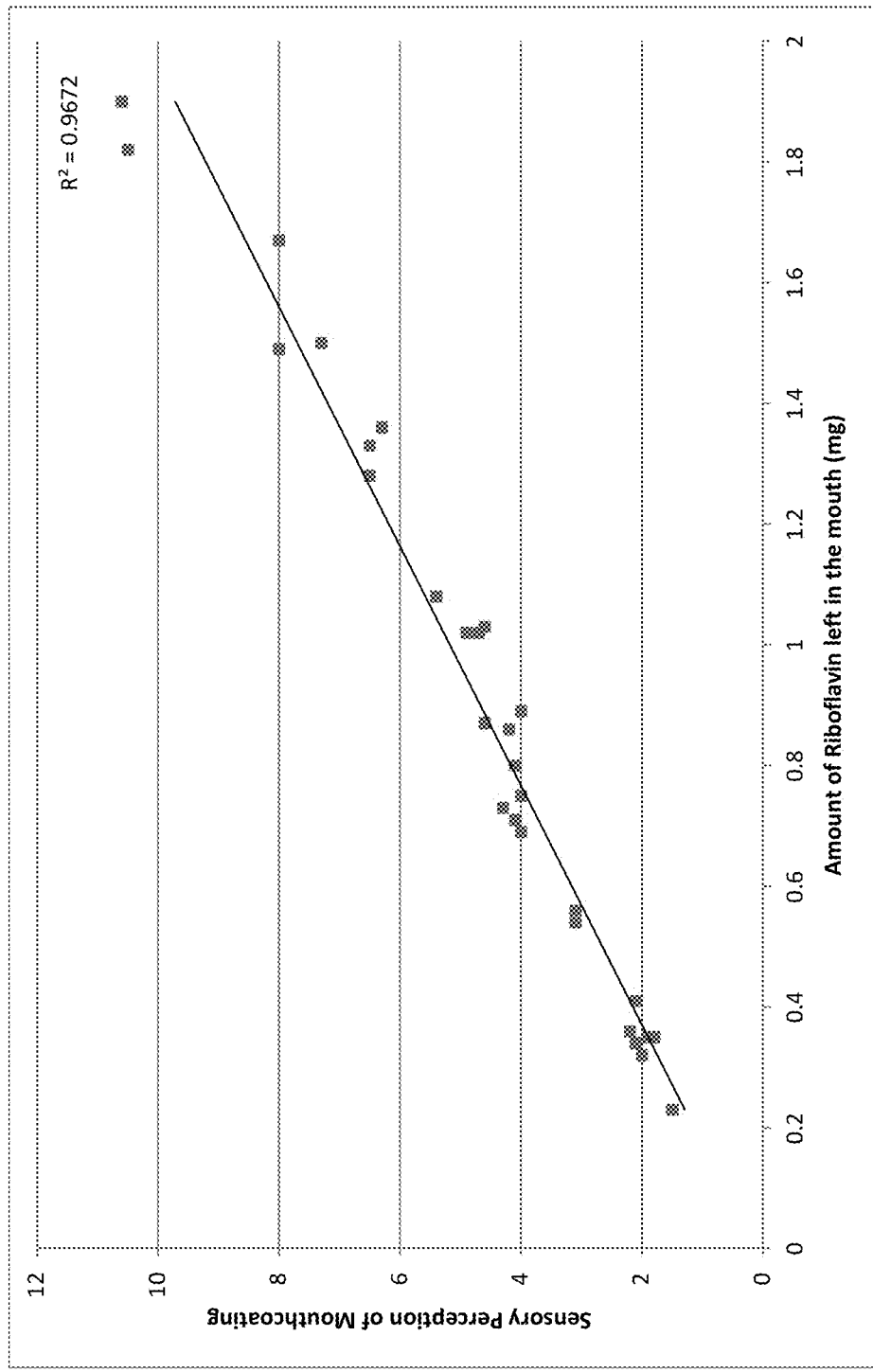
FIG. 11 is a graph depicting the linear relationship between the amount of riboflavin left in the mouth and the sensory perception of mouth-coating. See the Examples for complete details.

The amount of riboflavin left in the mouth was positively correlated with the sensory mouth-coating scores. A 1 mg increase in riboflavin corresponded to a 4.1 unit increase in the sensory perception of mouth-coating (p<0.001; FIG. 11). The amount of riboflavin left in the mouth plotted against the sensory mouthcoating scores showed a linear relationship as seen in FIG. 11. FIG. 11 shows the linear relationship between the amount of riboflavin left in the mouth and the sensory perception of mouth-coating. The points on the graph represent means for each nectar and thin honey beverage across all judges and all repetitions.

What is claimed is:

1. A method of providing sustenance to a dysphagic subject comprising feeding to the subject one or more edible compositions of matter having an apparent viscosity of from about 150 cP to about 2000 cP at about 30 s−1; a yield stress of from 0 Pa to about 20 Pa at 1 s$^{-1}$; and a flow index of from about 0.2 to about 0.6.

2. The method of claim 1, wherein the apparent viscosity of the edible composition is from about 200 cP to about 2000 cP, the yield stress is from 0 to about 15 pA, and the flow index is from about 0.3 to about 0.5.

3. The method of claim 1, wherein the apparent viscosity of the edible composition is from about 250 cP to about 1800 cP, the yield stress is from 5 to about 14 pA, and the flow index is from about 0.3 to about 0.5.

4. The method of claim 1, wherein the apparent viscosity of the edible composition is from about 250 cP to about 1800 cP, the yield stress is from 0 to about 2 pA, and the flow index is from about 0.3 to about 0.5.

5. The method of claim 1, wherein the apparent viscosity of the edible composition is from about 200 cP to about 500 cP, the yield stress is from 0 to about 2 Pa, and the flow index is from about 0.3 to about 0.5.

6. The method of claim 5, wherein the apparent viscosity of the edible composition is from about 250 cP to about 400 cP.

7. The method of claim 5, wherein the apparent viscosity of the edible composition is from about 270 cP to about 330 cP.

8. The method of claim 1, wherein the apparent viscosity of the edible composition is from about 1200 cP to about 1800 cP, the yield stress is from 5 to about 14 Pa, and the flow index is from about 0.3 to about 0.5.

9. The method of claim 8, wherein the apparent viscosity of the edible composition is from about 1250 cP to about 1700 cP.

10. The method of claim 8, wherein the apparent viscosity of the edible composition is from about 1400 cP to about 1600 cP.

* * * * *